(12) United States Patent
Kuo

(10) Patent No.: US 12,198,345 B2
(45) Date of Patent: Jan. 14, 2025

(54) NON-INVASIVE METHOD OF EVALUATING BLOOD CELL MEASUREMENT AND NON-INVASIVE BLOOD CELL MEASUREMENT EVALUATING SYSTEM

(71) Applicant: China Medical University, Taichung (TW)

(72) Inventor: Chin-Chi Kuo, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 453 days.

(21) Appl. No.: 17/734,608

(22) Filed: May 2, 2022

(65) Prior Publication Data

US 2022/0351382 A1 Nov. 3, 2022

(30) Foreign Application Priority Data

May 3, 2021 (TW) .................................. 110115926

(51) Int. Cl.
| | |
|---|---|
| G06T 7/00 | (2017.01) |
| A61B 5/145 | (2006.01) |
| G06T 5/90 | (2024.01) |
| G06T 7/90 | (2017.01) |
| G06V 10/774 | (2022.01) |
| G06V 10/776 | (2022.01) |
| G06V 20/69 | (2022.01) |

(52) U.S. Cl.
CPC ........ *G06T 7/0014* (2013.01); *A61B 5/14546* (2013.01); *G06T 5/90* (2024.01); *G06T 7/90* (2017.01); *G06V 10/774* (2022.01); *G06V 10/776* (2022.01); *G06V 20/698* (2022.01); *A61B 2576/02* (2013.01); *G06T 2207/20081* (2013.01); *G06T 2207/20132* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2017/0014035 A1* | 1/2017 | Newberry | ............... A61B 90/96 |
| 2022/0047223 A1* | 2/2022 | Gondi | ..................... G16H 30/40 |

FOREIGN PATENT DOCUMENTS

| | | | | |
|---|---|---|---|---|
| CN | 109738621 A | | 5/2019 | |
| CN | 112700859 A | | 4/2021 | |
| CN | 113705312 A | * | 11/2021 | |
| CN | 114929304 A | * | 8/2022 | .............. A61M 1/28 |
| TW | 201731460 A | | 9/2017 | |
| TW | 202115678 A | | 4/2021 | |

* cited by examiner

*Primary Examiner* — Fan Zhang

(57) ABSTRACT

A non-invasive method of evaluating blood cell measurement and a non-invasive blood cell measurement evaluating system are provided. The non-invasive method of evaluating blood cell measurement includes providing of a dialysis tubing image datum of a subject, performing an image preprocessing step, performing a model predicting step and performing a determining and classifying step. The non-invasive blood cell measurement evaluating system includes an image capturing device and a processor electrically connected to the image capture device.

19 Claims, 9 Drawing Sheets
(1 of 9 Drawing Sheet(s) Filed in Color)

NON-INVASIVE METHOD OF EVALUATING BLOOD CELL MEASUREMENT AND NON-INVASIVE BLOOD CELL MEASUREMENT EVALUATING SYSTEM

RELATED APPLICATIONS

This application claims priority to Taiwan Application Serial Number 110115926, filed May 3, 2021, which is herein incorporated by reference.

BACKGROUND

Technical Field

The present disclosure relates to a non-invasive method of evaluating blood cell measurement and an evaluating system thereof. More particularly, the present disclosure relates to a non-invasive method of evaluating blood cell measurement and an evaluating system thereof for evaluating a blood cell measurement value in blood or body fluid of a dialysis patient in real time.

Description of Related Art

Chronic kidney disease has become a global epidemic. In Taiwan, there are 1.5 million patients with kidney-related diseases, and patients with severe kidney-related diseases usually require renal replacement therapy as a treatment. Currently hemodialysis (commonly known as kidney dialysis) and peritoneal dialysis (commonly known as stomach dialysis) are the main renal replacement therapy.

However, long-term hemodialysis patients are prone to insufficient production of erythropoietin due to kidney damage, which in turn leads to low red blood cell counts and anemia, resulting in fatigue, lethargy, decreased appetite, decreased exercise capacity, and shortness of breath. Such symptoms may even lead to cardiovascular disease and death in the long run. On the other hand, peritoneal dialysis is an alternative dialysis method, and most peritoneal dialysis patients perform dialysis at home by themselves. However, if the dialysis tubing is contaminated with bacteria due to a poor operating environment or poor sterilization process, it will cause pathogens to enter the patient during peritoneal dialysis and cause infection. When infected, the dialysate will be cloudy due to the large number of white blood cells. Once infected with peritonitis, the patient must receive antibiotics, and severe infection may cause sepsis.

In fact, physician will regularly perform blood tests on patients undergoing hemodialysis to know the hemoglobin concentration in the patient's blood. When the hemoglobin concentration is lower than 10 g/dL, the physician may prescribe erythropoietin (EPO) according to the patient's condition to stabilize the hemoglobin concentration. However, not every time a patient comes to the hospital for hemodialysis, the physician should draw blood to check the patient's hemoglobin concentration. In addition to the fact that changes in hemoglobin concentration in the patient's blood cannot be detected in real time, the conventional method of blood testing by physician also imposes a burden on medical resources. More seriously, the critical condition such as severe anemia (hemoglobin less than 8 g/dL) or hemoglobin is too high under EPO treatment (hemoglobin greater than 12 g/dL) cannot be detected proactively based on conventional strategy of blood sampling and testing. On the other hand, peritoneal dialysis patients visit attending nephrologists on a monthly basis. If the patient has signs of infection or seeks medical attention due to an infection between the nephrology clinic visits, they must come back to the hospital and the white blood cell count in the patient's dialysate should be tested to confirm the patient's infection status. Peritoneal dialysis patients require up to four times a day of dialysis, and continued dialysis with early signs of infection may exacerbate the infection.

In view of this, it is an important development goal to develop a method and apparatus for measuring blood cells in blood or body fluids in real time without invasive blood testing methods such as blood drawing or bodily fluid sampling methods.

SUMMARY

According to one aspect of the present disclosure provides a non-invasive method of evaluating blood cell measurement including following steps. A dialysis tubing image datum of a subject is provided, wherein the dialysis tubing image datum includes a color correction image and a dialysis tubing image. An image preprocessing step is performed, wherein a color of the dialysis tubing image is corrected with the color correction image to obtain a processed dialysis tubing image datum. A model predicting step is performed, wherein a machine learning model is used to predict a blood cell measurement with the processed dialysis tubing image datum to obtain a blood cell measurement value. A determining and classifying step is performed, wherein the machine learning model is used to predict the blood cell measurement value and compare with a threshold to output a blood cell measurement evaluation result. The blood cell measurement value includes a hemoglobin concentration value and a white blood cell count, and the threshold includes a hemoglobin concentration threshold and a white blood cell count threshold. When the hemoglobin concentration value is less than or equal to the hemoglobin concentration threshold, the subject is determined to be required to undergo a relevant treatment to increase the hemoglobin concentration. When the hemoglobin concentration value is greater than the hemoglobin concentration threshold, the subject is determined not to be required to undergo the relevant treatment to increase the hemoglobin concentration, or to reduce or maintain an ongoing relevant treatment for increasing the hemoglobin concentration. When the white blood cell count is greater than or equal to the white blood cell count threshold, the subject is determined to be required to treat for infection.

According to another aspect of the present disclosure provides a non-invasive blood cell measurement evaluating system including an image capturing device and a processor. The image capturing device is for obtaining a dialysis tubing image datum of a subject, wherein the dialysis tubing image datum includes a color correction image and a dialysis tubing image. The processor is electrically connected to the image capture device, and includes an image correcting program and a machine learning model. The image correcting program includes an image correcting module for correcting a color of the dialysis tubing image by the color correction image to obtain a processed dialysis tubing image datum. The machine learning model is electrically connected to the image correcting program, and includes a value predicting unit and an evaluating unit. The value predicting unit uses the processed dialysis tubing image datum to predict a blood cell measurement, so as to obtain a blood cell measurement value. The evaluating unit predicts the blood cell measurement value and compares with a threshold to output a blood cell measurement evaluation result. The blood cell measurement value includes a hemoglobin concentration value and a white blood cell count, and the threshold includes a hemoglobin concentration threshold and a white blood cell count threshold. When the hemoglobin concentration value is less than or equal to the hemoglobin concentration threshold, the subject is determined to be required to undergo a relevant treatment to increase the hemoglobin concentration. When the hemoglobin concentration value is greater than the hemoglobin concentration threshold, the subject is determined not to be required to undergo the relevant treatment to increase the hemoglobin concentration, or to reduce or maintain an ongoing relevant treatment for increasing the hemoglobin concentration. When the white blood cell count is greater than or equal to the white blood cell count threshold, the subject is determined to be required to treat for infection.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Reference will now be made in detail to the present embodiments of the present disclosure, examples of which are illustrated in the accompanying drawings.

Figure 1:
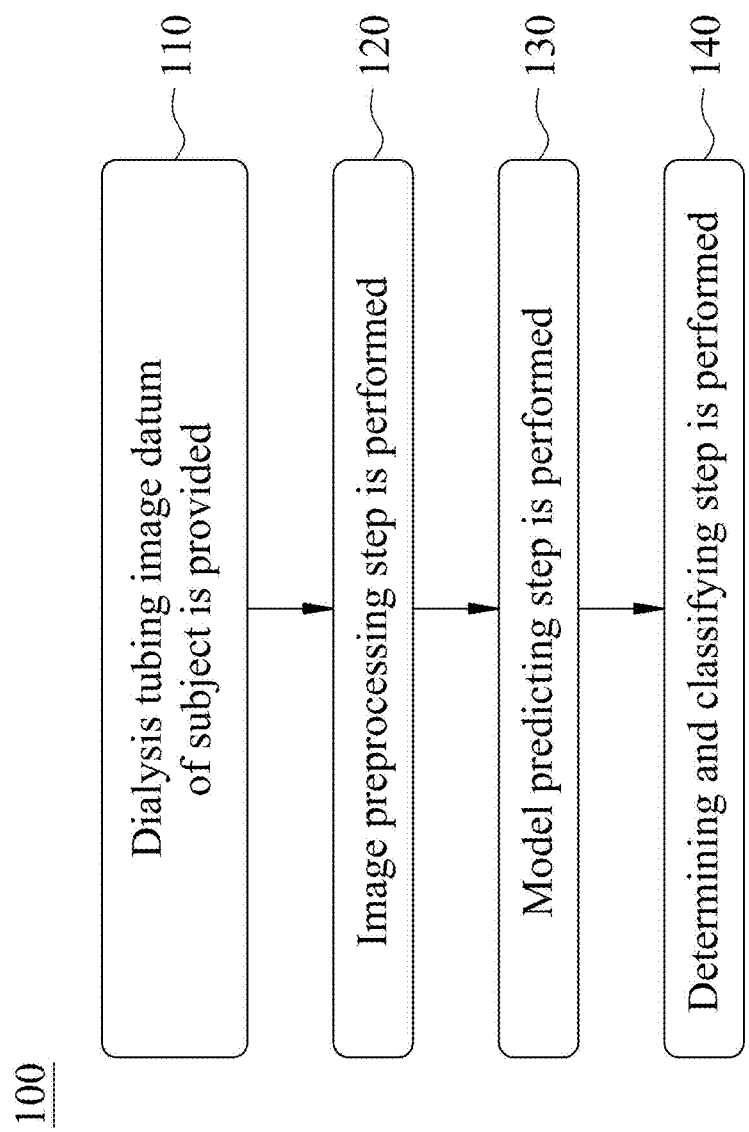
FIG. 1 is a flowchart of a non-invasive method of evaluating blood cell measurement according to 1st example of one embodiment of the present disclosure.
Figure 2:
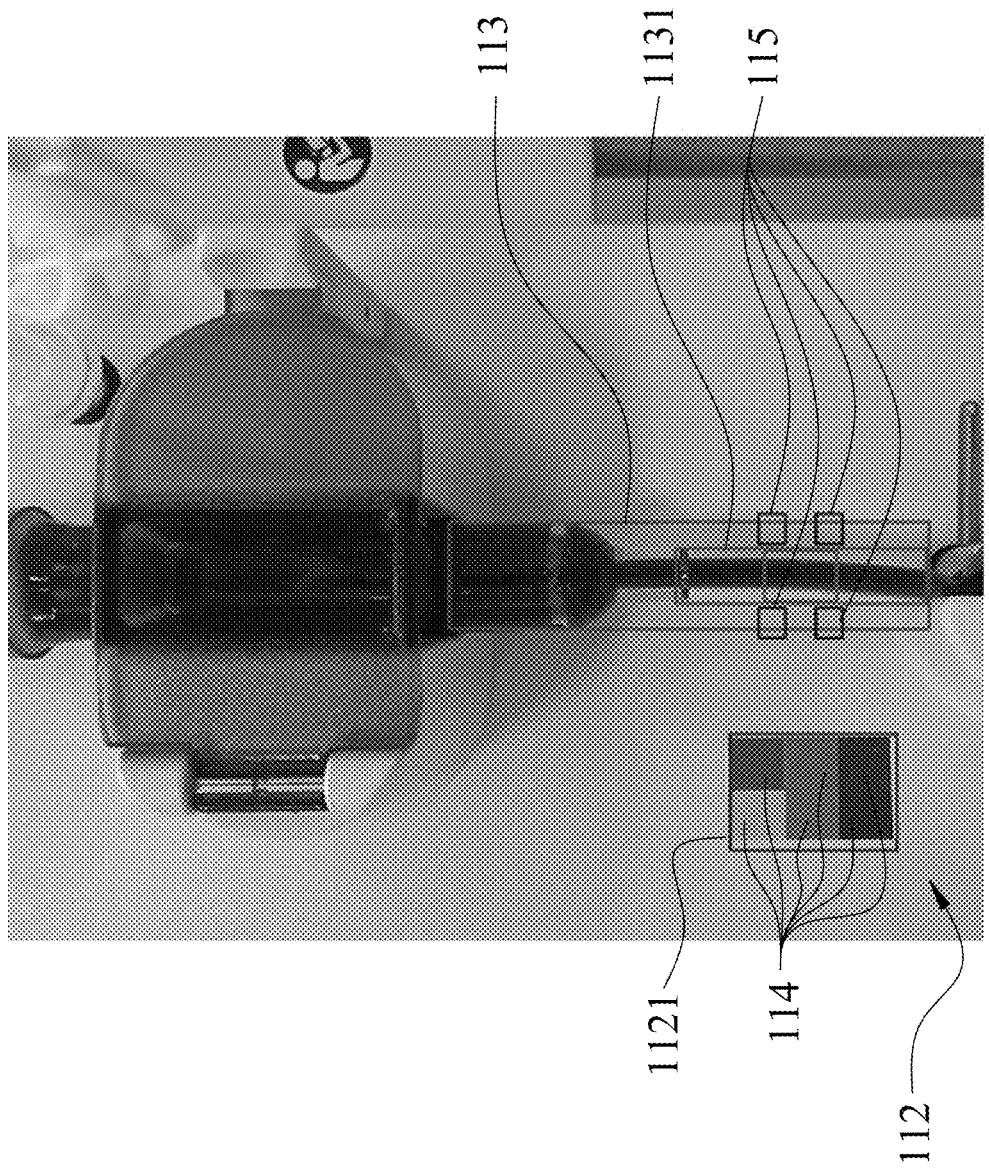
FIG. 2 is a photographic image of a dialysis tubing image datum according to the present disclosure.

Please refer to FIG. 1 and FIG. 2. FIG. 1 is a flowchart of a non-invasive method of evaluating blood cell measurement 100 according to 1st example of one embodiment of the present disclosure. FIG. 2 is a photographic image of a dialysis tubing image datum 111 according to the present disclosure. The non-invasive method of evaluating blood cell measurement 100 includes Step 110, Step 120, Step 130 and Step 140.

In Step 110, a dialysis tubing image datum 111 of a subject is provided. As shown in FIG. 2, the dialysis tubing image datum 111 includes a color correction image 112 and a dialysis tubing image 113. In detail, the dialysis tubing image datum 111 can be obtained by capturing picture with a mobile device. When capturing the dialysis tubing image datum 111, the placement position of the color correction image 112 does not need to be precise. In particular, the color correction image 112 can be a color card, and the color correction image 112 includes at least one contrasting color 114, which is used to specifically compare information such as brightness, saturation, and color of the environment during capturing. In FIG. 2, the color correction image 112 can include six contrasting colors 114, the colors of which can be red, blue, green, 20% grayscale, 50% grayscale, and 80% grayscale.

Further, although the dialysis tubing image 113 shown in FIG. 2 is an image of a dialysis tubing image of hemodialysis, the non-invasive method of evaluating blood cell measurement 100 can also be applied to peritoneal dialysis, and a dialysis tubing image of peritoneal dialysis can be used as the dialysis tubing image 113 to perform Step 110.

In Step 120, an image preprocessing step is performed, wherein a color of the dialysis tubing image 113 is corrected with the color correction image 112 to obtain a processed dialysis tubing image datum (not shown).

In detail, the image preprocessing step can further include cropping the color correction image 112 and the dialysis tubing image 113 along edges thereof to obtain a cropped color correction image 1121 and a cropped dialysis tubing image 1131. Then the cropped color correction image 1121 is used to correct the cropped dialysis tubing image 1131 to improve model prediction accuracy.

In addition, the image preprocessing step can further include a background correction for reducing ambient light source differences in the dialysis tubing image 113, which is to select two positions on the left and right sides of the dialysis tubing image 113 and near the dialysis tube for cropping to obtain four cropped background images 115. The ambient light source differences in the dialysis tubing image 113 can be reduced and standardized by the cropped background images 115 to improve model prediction accuracy and ensure the evaluation consistency and correctness of the non-invasive method of evaluating blood cell measurement 100 of the present disclosure.

In Step 130, a model predicting step is performed, wherein a machine learning model is used to predict a blood cell measurement with the processed dialysis tubing image datum to obtain a blood cell measurement value.

In addition, the non-invasive method of evaluating blood cell measurement 100 can further include providing a previous blood cell measurement value from previous blood test report (not shown). The previous blood cell measurement value is used as a parameter for predicting the blood cell measurement with the processed dialysis tubing image datum in the image preprocessing step, so as to improve the evaluation accuracy of the non-invasive method of evaluating blood cell measurement 100 of the present disclosure.

In Step 140, a determining and classifying step is performed. The machine learning model is used to predict the blood cell measurement value and compare with a threshold to output a blood cell measurement evaluation result. In detail, the blood cell measurement value includes a hemoglobin concentration value and a white blood cell count, and the threshold includes a hemoglobin concentration threshold and a white blood cell count threshold, wherein the blood cell measurement values correspond to the corresponding thresholds respectively. In term of the hemoglobin concentration value, when the hemoglobin concentration value is less than or equal to the hemoglobin concentration threshold, the subject is determined to be required to undergo a relevant treatment to increase the hemoglobin concentration, such as increasing a dose of erythropoietin. When the hemoglobin concentration value is greater than the hemoglobin concentration threshold, the subject is determined not to be required to undergo the relevant treatment to increase the hemoglobin concentration, or to reduce or maintain an ongoing relevant treatment for increasing the hemoglobin concentration, for example, there is no need to adjust or adjust the dose of erythropoietin. The hemoglobin concentration threshold can be 10 g/dL. In term of the white blood cell count, when the white blood cell count is greater than or equal to the white blood cell count threshold, the subject is determined to be required to treat for infection, for example, providing the subject with drugs such as antibiotics. When the white blood cell count is less than the white blood cell count threshold indicating that the subject is not likely to be infected, the subject is determined not to be required to treat for infection. The white blood cell count threshold can be 100 cells/mm$^3$.

Therefore, the non-invasive method of evaluating blood cell measurement 100 can achieve the effect of non-invasive and non-contact real-time detection of blood cell measurement in blood or body fluids, and can intuitively enable medical staff to decide the subsequent treatment.

Figure 3:
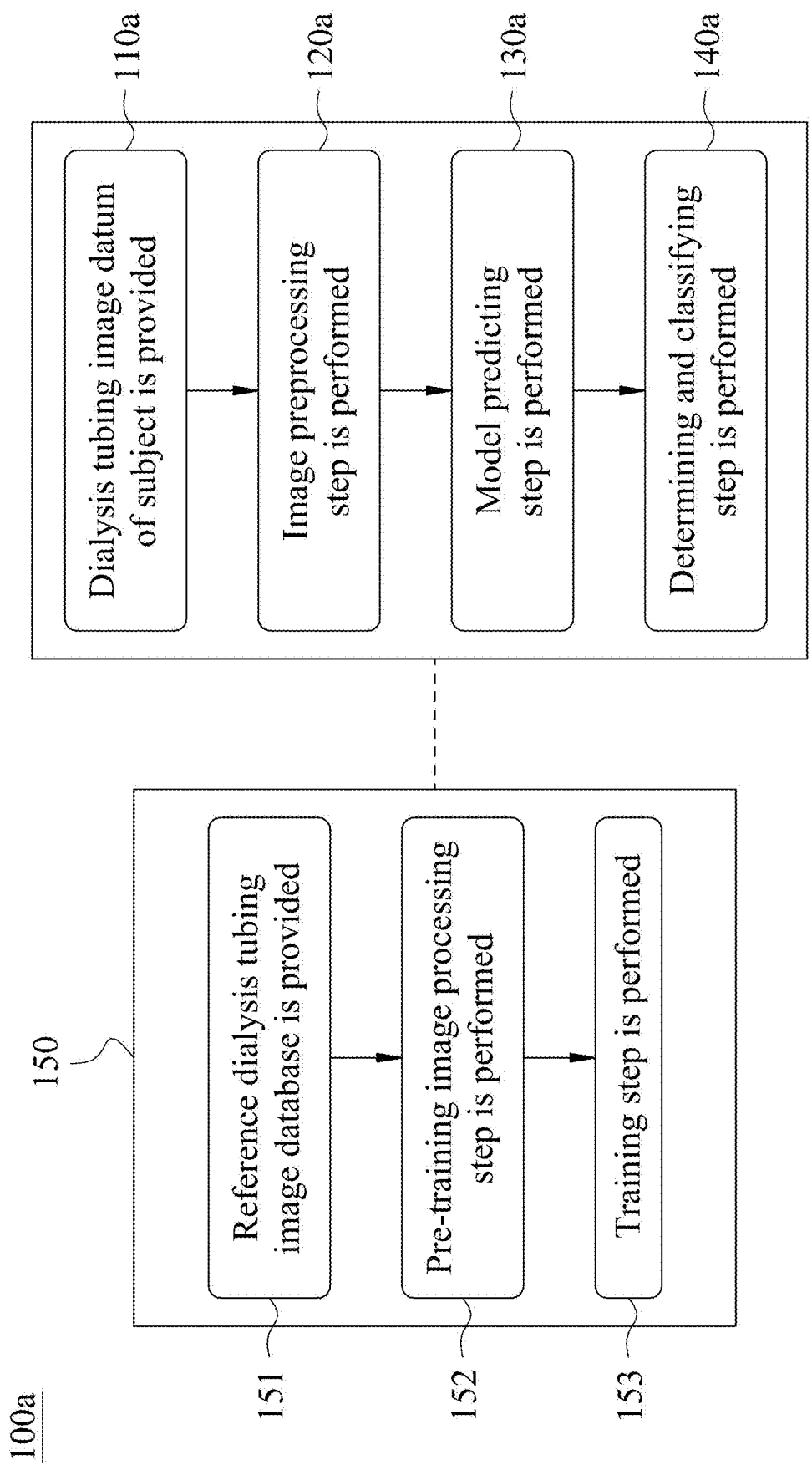
FIG. 3 is a flowchart of a non-invasive method of evaluating blood cell measurement according to 2nd example of one embodiment of the present disclosure.

Please further refer to FIG. 1 and FIG. 3. FIG. 3 is a flowchart of a non-invasive method of evaluating blood cell measurement 100a according to 2nd example of one embodiment of the present disclosure. The non-invasive method of evaluating blood cell measurement 100a includes Step 110a, Step 120a, Step 130a, Step 140a and Step 150, wherein Step 110a, Step 120a, Step 130a, and Step 140a are the same as Step 110, Step 120, Step 130, and Step 140 in FIG. 1, and will not be repeated here. Establishment details of a machine learning model of the present disclosure will be described below with reference to FIG. 1 and FIG. 3. Step 150 is a model building step, which includes Step 151, Step 152 and Step 153.

In Step 151, a reference dialysis tubing image database is provided. The reference dialysis tubing image database includes a plurality of reference dialysis tubing image data, and each of the reference dialysis tubing image data includes a reference color correction image and a reference dialysis tubing image, wherein format of reference color correction image is same as the color correction image, and format of the reference dialysis tubing image is same as the dialysis tubing image. In detail, the reference dialysis tubing image data can be obtained through the camera of mobile device. When capturing each of the reference dialysis tubing images, the placement position of the reference color correction image does not need to be precise. In particular, the reference color correction image can include at least one contrasting color, wherein a number of the contrasting color can be six, and the colors of the contrasting colors can be red, blue, green, 20% grayscale, 50% grayscale, and 80% grayscale. The color and color arrangement of the reference color correction image can also be the same as the color correction image 112 in FIG. 2, but the present disclosure is not limited to this.

In Step 152, a pre-training image processing step is performed, wherein a color of the reference dialysis tubing image is corrected with the reference color correction image to obtain a plurality of reference processed dialysis tubing image data.

In detail, the pre-training image processing step can further include cropping the reference color correction image and the reference dialysis tubing image along edges thereof to obtain a reference cropped color correction image and a reference cropped dialysis tubing image. Then the reference cropped color correction image is used to correct the reference cropped dialysis tubing image to improve model prediction accuracy.

In addition, the pre-training image processing step can further include a background correction for reducing ambient light source differences in the reference dialysis tubing image, which is to select two positions on the left and right sides of the reference dialysis tubing image and near the dialysis tube for cropping to obtain four reference cropped background images. The ambient light source differences in the reference dialysis tubing image can be reduced and standardized by the reference cropped background images to improve model prediction accuracy and ensure the evaluation consistency and correctness of the non-invasive method of evaluating blood cell measurement 100a of the present disclosure.

In Step 153, a training step is performed, wherein a machine learning algorithm module is trained with the reference processed dialysis tubing image data until a loss function converge to obtain an optimal machine learning model. The machine learning algorithm module can be a gradient descent algorithm. Preferably, the machine learning algorithm module can be XGBoost algorithm module, but the present disclosure is not limited to this.

In detail, the non-invasive method of evaluating blood cell measurement 100a can further include providing a previous reference blood cell measurement value from previous blood test report (not shown). The previous reference blood cell measurement value is used as a parameter for training the machine learning algorithm module with the reference processed dialysis tubing image data in the pre-training image processing step.

Figure 4:
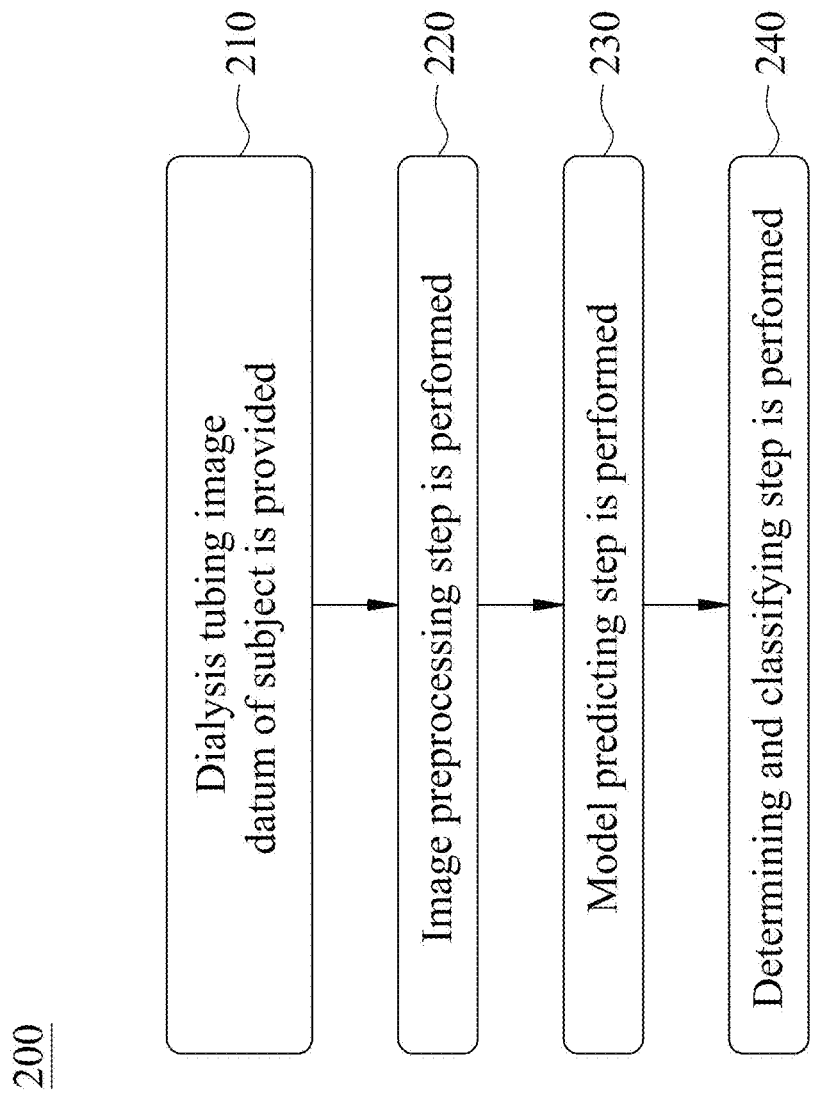
FIG. 4 is a flowchart of a non-invasive method of evaluating blood cell measurement according to 3rd example of one embodiment of the present disclosure.

Please refer to FIG. 4, which is a flowchart of a non-invasive method of evaluating blood cell measurement 200 according to 3rd example of one embodiment of the present disclosure. The non-invasive method of evaluating blood cell measurement 200 includes Step 210, Step 220, Step 230 and Step 240, wherein Step 210, Step 230, and Step 240 are the same as Step 110, Step 130, and Step 140 in FIG. 1, and will not be repeated here.

In Step 220, an image preprocessing step is performed, which is based on the same basis as Step 120, and then uses a statistical distribution model of a color histogram to describe a feature of the processed dialysis tubing image data. The same part as Step 120 will not be repeated here. In detail, the processed dialysis tubing image data is adjusted by the color histogram averaging and transferred the feature to the color gradation distribution, so as to further reduce the influence of the ambient light source differences in the dialysis tubing image datum of the subject when capturing the dialysis tubing image datum, and ensure the evaluation consistency and correctness of the non-invasive method of evaluating blood cell measurement 200 of the present disclosure.

Figure 5:
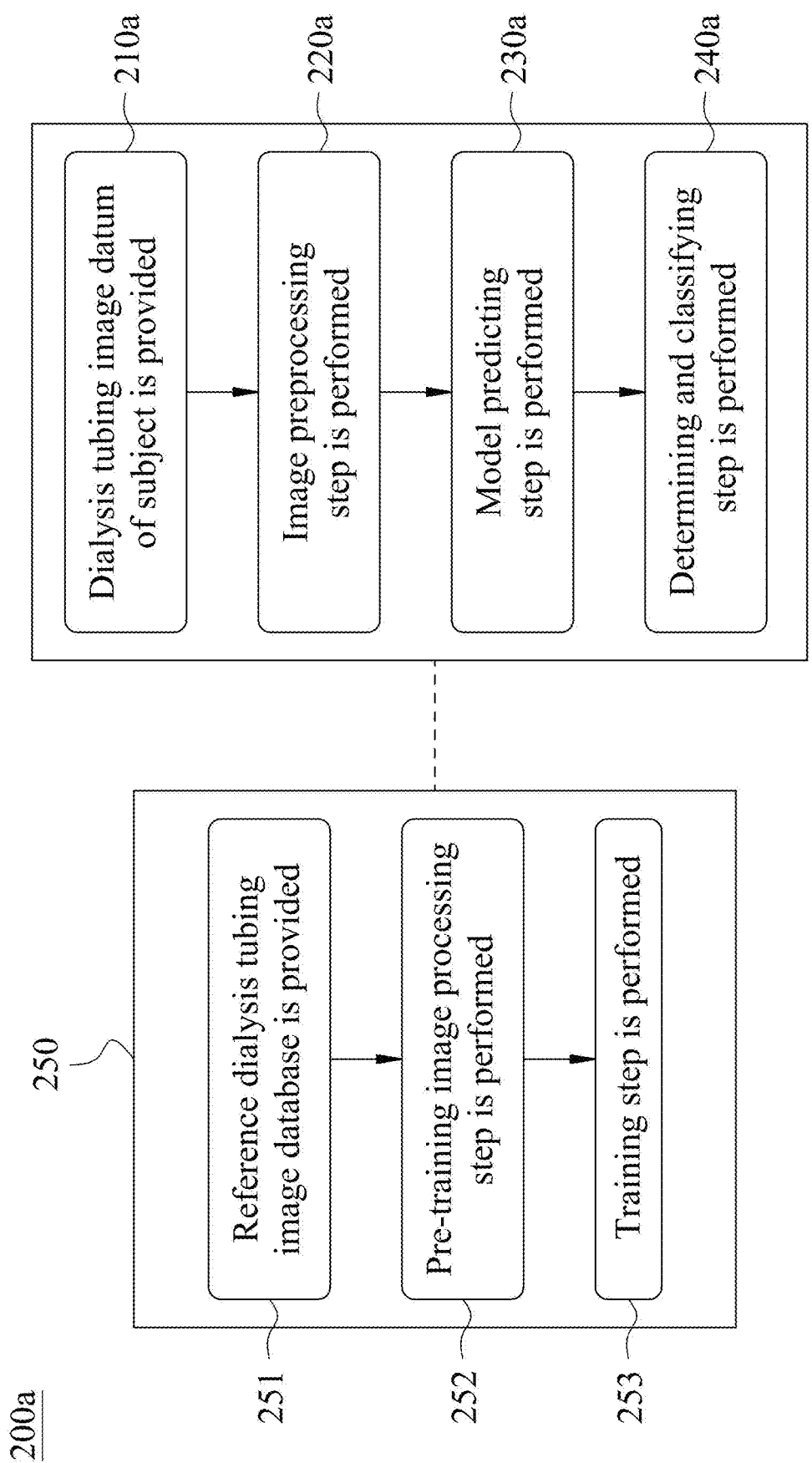
FIG. 5 is a flowchart of a non-invasive method of evaluating blood cell measurement according to 4th example of one embodiment of the present disclosure.

Please further refer to FIG. 4 and FIG. 5. FIG. 5 is a flowchart of a non-invasive method of evaluating blood cell measurement 200a according to 4th example of one embodiment of the present disclosure. The non-invasive method of evaluating blood cell measurement 200a includes Step 210a, Step 220a, Step 230a, Step 240a and Step 250, wherein Step 210a, Step 220a, Step 230a, and Step 240a are the same as Step 210, Step 220, Step 230, and Step 240 in FIG. 4, and will not be repeated here. Establishment details of a machine learning model of the present disclosure will be described below with reference to FIG. 4 and FIG. 5. Step 250 is a model building step, which includes Step 251, Step 252 and Step 253. Step 251 and Step 253 are the same as Step 151 and Step 153 in FIG. 3, and will not be repeated here.

In Step 252, a pre-training image processing step is performed, which is based on the same basis as Step 152, and then further crops each of the reference processed dialysis tubing image data with a second cropping range. The same part as Step 152 will not be repeated here. In detail, the second cropping range can be an area with a width of 3 pixels in the middle of the reference processed dialysis tubing image datum, so as to further reduce the influence of the ambient light source differences in the reference dialysis tubing image datum of the subjects when capturing the reference dialysis tubing image datum, and ensure the evaluation consistency and correctness of the non-invasive method of evaluating blood cell measurement 200a of the present disclosure.

Figure 6:
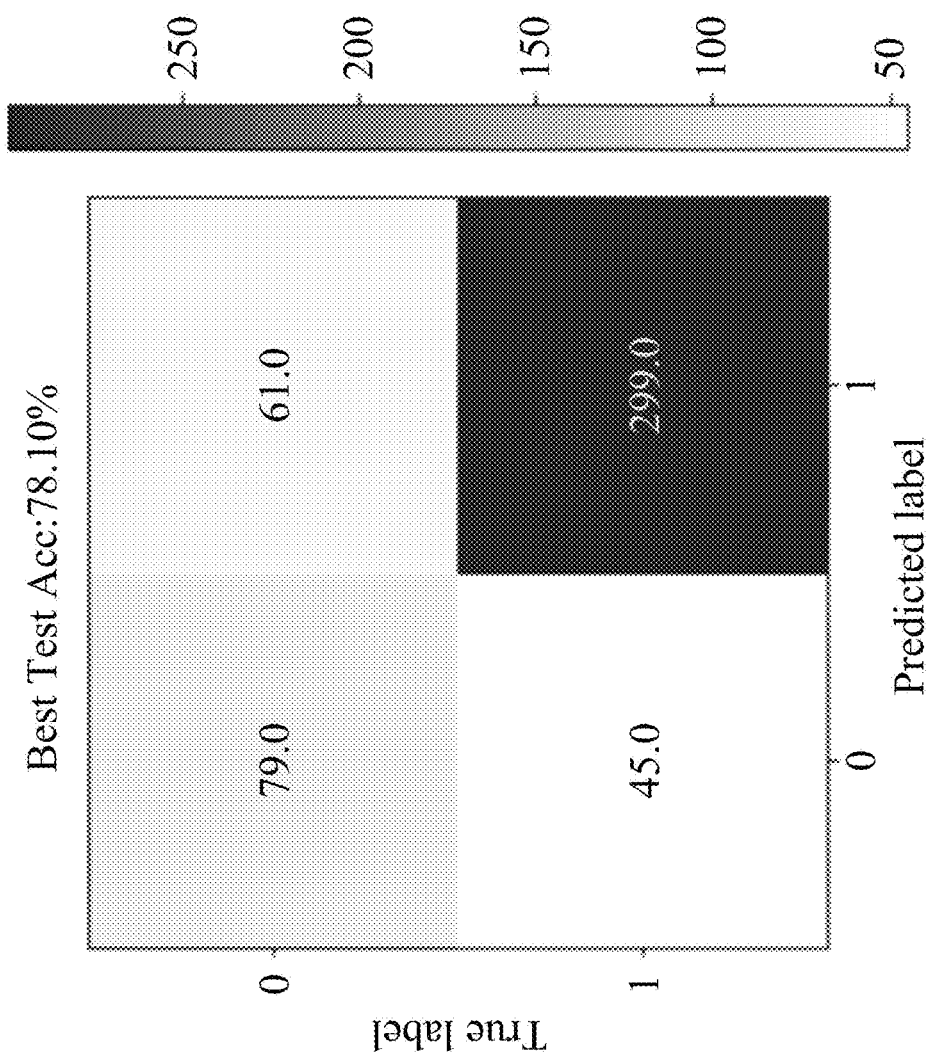
FIG. 6 shows accuracy performance results of the non-invasive method of evaluating blood cell measurement according to the 1st example and the 2nd example of the present disclosure.
Figure 7:
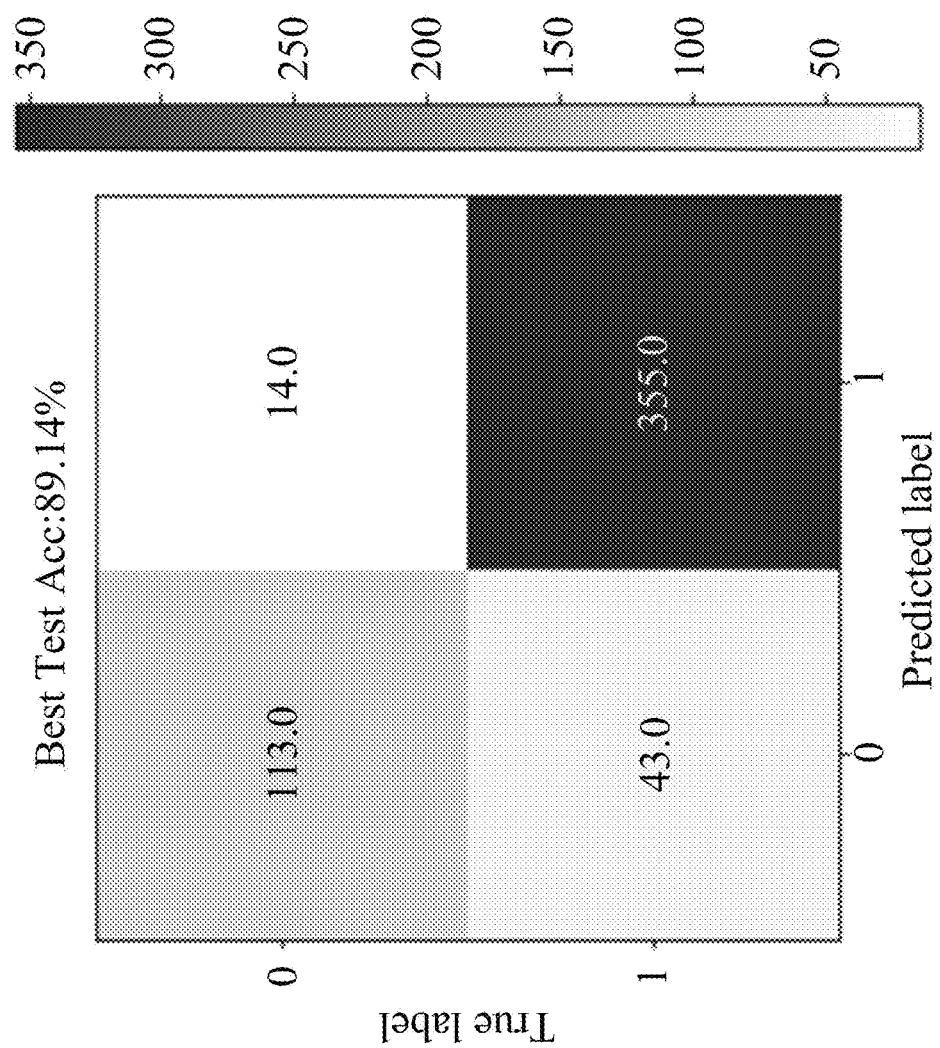
FIG. 7 shows accuracy performance results of the non-invasive method of evaluating blood cell measurement according to the 3rd example and the 4th example of the present disclosure.

Please refer to FIG. 6 and FIG. 7. FIG. 6 shows accuracy performance results of the non-invasive method of evaluating blood cell measurement according to the 1st example and the 2nd example of the present disclosure. FIG. 7 shows accuracy performance results of the non-invasive method of evaluating blood cell measurement according to the 3rd example and the 4th example of the present disclosure. In FIG. 6 and FIG. 7 the subject to be determined is the hemoglobin concentration in the blood cell measurement. The X-axis represents the evaluation result of the subject's hemoglobin concentration predicted by the machine learning model, wherein 0 on the X-axis represents that the predicted value of hemoglobin concentration is less than or equal to the hemoglobin concentration threshold, and 1 on the X-axis represents that the predicted value of hemoglobin concentration is greater than the hemoglobin concentration threshold. The Y-axis represents the evaluation result of the hemoglobin concentration obtained by the subject through the blood test, wherein 0 on the Y-axis represents that the actual value of the hemoglobin concentration is less than or equal to the hemoglobin concentration threshold, and 1 on the Y-axis represents the actual hemoglobin concentration greater than the hemoglobin concentration threshold. The aforementioned hemoglobin concentration threshold is 10 g/dL.

In detail, when (X, Y) is (0, 0), it means that the evaluation result of the subject's hemoglobin concentration by the machine learning model is consistent with the blood test result, so it is classified as an accurate prediction, and the evaluation result is that the subject is required to undergo a relevant treatment to increase the hemoglobin concentration. When (X, Y) is (1, 0) or (0, 1), it means that the evaluation result of the subject's hemoglobin concentration by the machine learning model is inconsistent with the blood test result, so it is classified as an inaccurate prediction. When (X, Y) is (1, 1), it means that the evaluation result of the subject's hemoglobin concentration by the machine learning model is consistent with the blood test result, so it is classified as an accurate prediction, and the evaluation result is that the subject is not required to undergo the relevant treatment to increase the hemoglobin concentration, or can reduce or maintain the ongoing relevant treatment for increasing the hemoglobin concentration. In FIG. 6, it can be calculated that among the 484 subjects, 378 subjects are accurately predicted, so the accuracy of the non-invasive method of evaluating blood cell measurement according to the 1st example and the 2nd example of the present disclosure is 78.10%. In FIG. 7, it can be calculated that among the 525 subjects, 468 subjects are accurately predicted, so the accuracy of the non-invasive method of evaluating blood cell measurement according to the 3rd example and the 4th example of the present disclosure is 89.14%.

Further, due to the high accuracy of the non-invasive method of evaluating blood cell measurement of the present disclosure, medical staff can perform subsequent medical treatment through the evaluation result of the non-invasive method of evaluating blood cell measurement of the present disclosure. For the evaluation result of the hemoglobin concentration in the previous paragraph, when the subject is determined to be required to undergo the relevant treatment to increase the hemoglobin concentration, the medical staff can increase the dose of erythropoietin required by the subject based on the evaluation result. One the other hand, when the subject is determined not to be required to undergo the relevant treatment to increase the hemoglobin concentration, or to reduce or maintain the ongoing relevant treatment for increasing the hemoglobin concentration, the medical staff can maintain or reduce the dose of erythropoietin required by the subject based on the evaluation result. Therefore, compared with the conventional method of drawing blood for testing blood cell measurement, the non-invasive method of evaluating blood cell measurement of the present disclosure can evaluate blood cell measurement more quickly, so that medical staff can make subsequent treatment, so it can greatly reduce the consumption of time and medical resources.

Although in FIGS. 6 and 7, the hemoglobin concentration threshold is 10 g/dL, but the setting of the hemoglobin concentration threshold can be adjusted according to the actual application situation and the needs of each subject. The present disclosure is not limited to this. In addition, the target determined in FIGS. 6 and 7 is the hemoglobin concentration in the blood cell measurement, but other values included in the blood cell measurement, such as the white blood cell count, can also be evaluated in the same way through the selection of the corresponding threshold through the machine learning model, and it is not repeated here.

Therefore, the non-invasive method of evaluating blood cell measurement of the present disclosure is to perform image preprocessing on the dialysis tubing image datum and use the machine learning algorithm module to train to convergence. Then the machine learning model trained by the machine learning algorithm module is used to analyze and evaluate the dialysis tubing image datum. In this way, it can not only provide a fast and accurate non-invasive examination method for evaluating blood cell measurement based on the dialysis tubing image datum, but also avoid the burden of medical resources caused by the need for medical personnel to draw blood in the conventional evaluating blood cell measurement.

Figure 8:
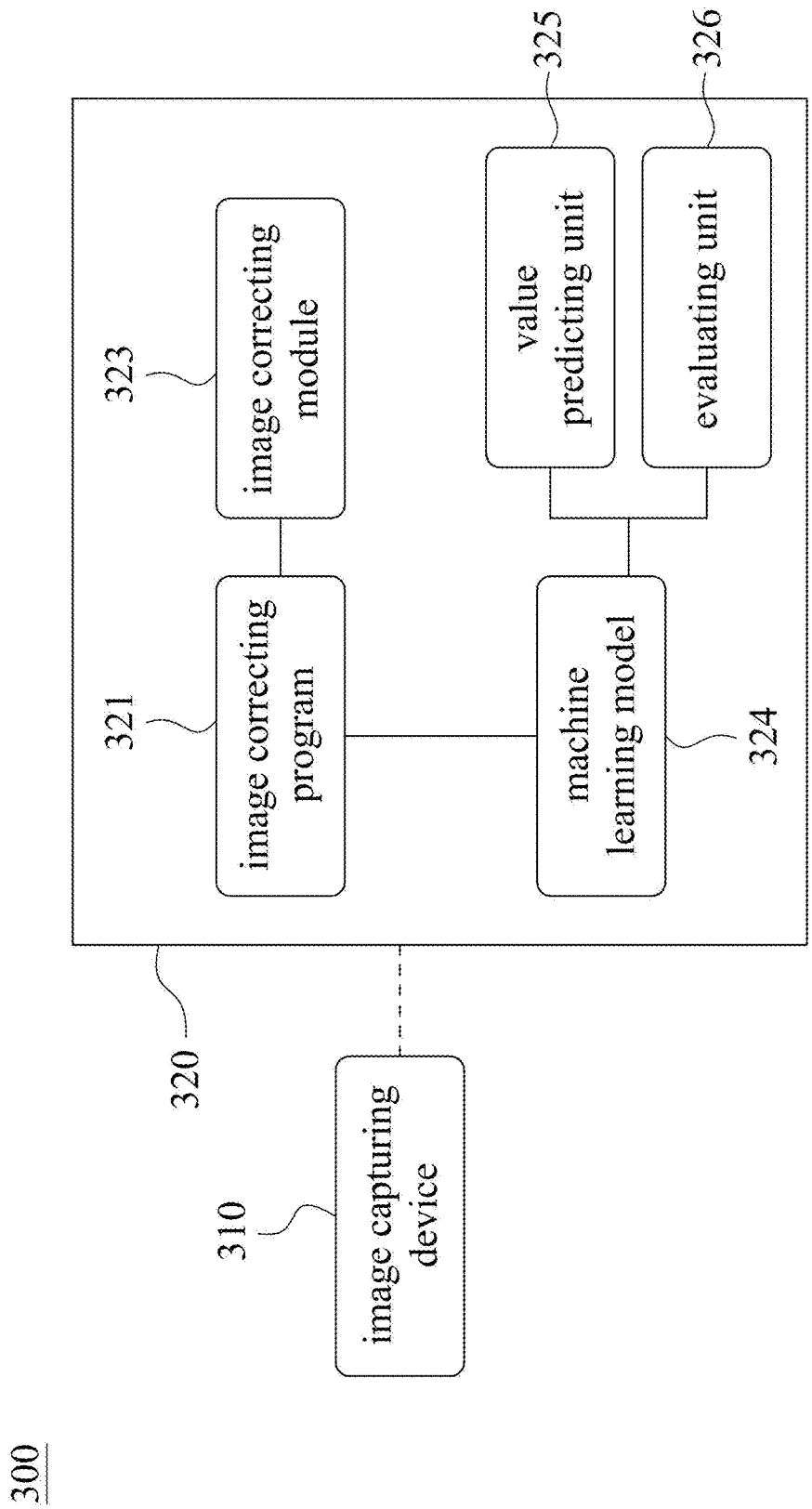
FIG. 8 is a schematic view of a non-invasive blood cell measurement evaluating system according to one example of another embodiment of the present disclosure.

Please refer to FIG. 8, which is a schematic view of a non-invasive blood cell measurement evaluating system 300 according to one example of another embodiment of the present disclosure. The non-invasive blood cell measurement evaluating system 300 includes an image capturing device 310 and a processor 320. The image capturing device 310 is for obtaining a dialysis tubing image datum of a subject. The dialysis tubing image datum includes a color correction image and a dialysis tubing image. The processor 320 is electrically connected to the image capture device 310, and includes an image correcting program 321 and a machine learning model 324. The image correcting program 321 includes an image correcting module 323 for correcting a color of the dialysis tubing image by the color correction image to obtain a processed dialysis tubing image datum. In detail, the image correcting module 323 can further reduce an ambient light source differences in the dialysis tubing image, but the present disclosure is not limited to this. The machine learning model 324 is electrically connected to the image correcting program 321, and includes a value predicting unit 325 and an evaluating unit 326. The value predicting unit 325 uses the processed dialysis tubing image datum to predict a blood cell measurement, so as to obtain a blood cell measurement value. The evaluating unit 326 compares the blood cell measurement value with a threshold to output a blood cell measurement evaluation result. In detail, the blood cell measurement value includes a hemoglobin concentration value and a white blood cell count, and the threshold includes a hemoglobin concentration threshold and a white blood cell count threshold, wherein the blood cell measurement values correspond to the corresponding thresholds respectively. In term of the hemoglobin concentration value, when the hemoglobin concentration value is less than or equal to the hemoglobin concentration threshold, the subject is determined to be required to undergo a relevant treatment to increase the hemoglobin concentration; when the hemoglobin concentration value is greater than the hemoglobin concentration threshold, the subject is determined not to be required to undergo the relevant treatment to increase the hemoglobin concentration or to reduce or maintain an ongoing relevant treatment for increasing the hemoglobin concentration. The hemoglobin concentration threshold can be 10 g/dL. In term of the white blood cell count, when the white blood cell count is greater than or equal to the white blood cell count threshold, the subject is determined to be required to treat for infection. When the white blood cell count is less than the white blood cell count threshold indicating that the subject is not infected, the subject is determined not to be required to treat for infection. The white blood cell count threshold can be 100 cells/mm$^3$.

In detail, the image capturing device 310 can be a mobile device installed with an application of the non-invasive blood cell measurement evaluating system 300.

In detail, the machine learning model 324 is trained by a machine learning algorithm module. The machine learning algorithm module can be a gradient descent algorithm. Preferably, the machine learning algorithm module can be XGBoost algorithm module.

Therefore, the non-invasive blood cell measurement evaluating system 300 can achieve the effect of non-invasive and non-contact real-time detection of blood cell measurement in blood or body fluids, and can intuitively enable medical staff to decide the subsequent treatment.

Figure 9:
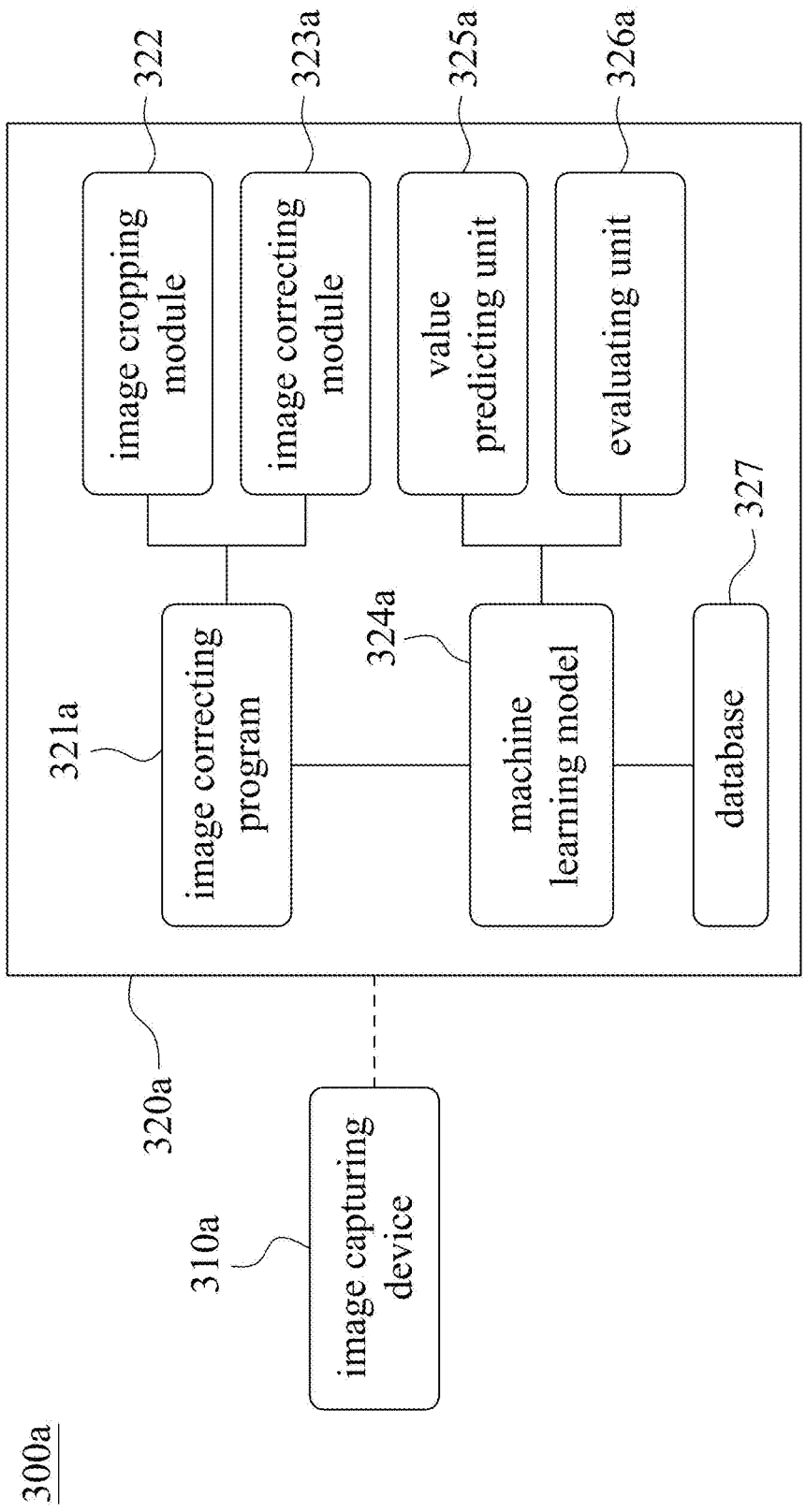
FIG. 9 is a schematic view of a non-invasive blood cell measurement evaluating system according to another example of another embodiment of the present disclosure.

Please refer to FIG. 9, which is a schematic view of a non-invasive blood cell measurement evaluating system 300a according to another example of another embodiment of the present disclosure. The non-invasive blood cell measurement evaluating system 300a includes an image capturing device 310a and a processor 320a. The processor 320a includes an image correcting program 321a, a machine learning model 324a and a database 327. The image correcting program 321a includes an image cropping module 322 and an image correcting module 323a. The machine learning model 324a includes a value predicting unit 325a and an evaluating unit 326a. The image capturing device 310a, the image correcting module 323a, the machine learning model 324a, the value predicting unit 325a and the evaluating unit 326a of the non-invasive blood cell measurement evaluating system 300a are the same as the image capturing device 310, the image correcting module 323, the machine learning model 324, the value predicting unit 325 and the evaluating unit 326 of the non-invasive blood cell measurement evaluating system 300 in FIG. 8, and will not be repeated here.

In detail, the image correcting program 321a further includes the image cropping module 322 for cropping a color correction image and a dialysis tubing image along edges thereof, so as to obtain a cropped color correction image and a cropped dialysis tubing image. Then the cropped color correction image is used to correct the cropped dialysis tubing image to improve model prediction accuracy.

The image cropping module 322 can further describe a feature of the processed dialysis tubing image datum by a statistical distribution model of a color histogram. In detail, the processed dialysis tubing image datum is adjusted by the color histogram averaging and transferred the feature to the color gradation distribution.

More particularly, the processor 320a can further include the database 327 including a previous blood cell measurement value from previous blood test report. The machine learning model 324a can use the previous blood cell measurement value as a parameter to predict the blood cell measurement with the processed dialysis tubing image datum to obtain a more accurate prediction result.

To sum up, the non-invasive blood cell measurement evaluating system of the present disclosure can use the dialysis tubing image datum taken during the dialysis process to output the prediction result immediately after the being cropped, corrected, predicted and determined by the processor for the reference of patients and doctors. Thereby, subsequent treatment can be made in real time based on the prediction results, reducing the waste of medical resources and time, and ensuring the health of patients.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. A non-invasive method of evaluating blood cell measurement, comprising:
providing of a dialysis tubing image datum of a subject, wherein the dialysis tubing image datum comprises a color correction image and a dialysis tubing image;
performing an image preprocessing step, wherein a color of the dialysis tubing image is corrected with the color correction image to obtain a processed dialysis tubing image datum;
performing a model predicting step, wherein a machine learning model is used to predict a blood cell measurement with the processed dialysis tubing image datum to obtain a blood cell measurement value; and
performing a determining and classifying step, wherein the machine learning model is used to predict the blood cell measurement value and compare with a threshold to output a blood cell measurement evaluation result;
wherein the blood cell measurement value comprises a hemoglobin concentration value and a white blood cell count, and the threshold comprises a hemoglobin concentration threshold and a white blood cell count threshold;

when the hemoglobin concentration value is less than or equal to the hemoglobin concentration threshold, the subject is determined to be required to undergo a relevant treatment to increase the hemoglobin concentration, and when the hemoglobin concentration value is greater than the hemoglobin concentration threshold, the subject is determined not to be required to undergo the relevant treatment to increase the hemoglobin concentration, or to reduce or maintain an ongoing relevant treatment for increasing the hemoglobin concentration; and when the white blood cell count is greater than or equal to the white blood cell count threshold, the subject is determined to be required to treat for infection.

2. The non-invasive method of evaluating blood cell measurement of claim 1, wherein the color correction image comprises at least one contrasting color.

3. The non-invasive method of evaluating blood cell measurement of claim 1, wherein the image preprocessing step further comprises cropping the color correction image and the dialysis tubing image along edges thereof.

4. The non-invasive method of evaluating blood cell measurement of claim 1, wherein the image preprocessing step further comprises a background correction for reducing ambient light source differences in the dialysis tubing image.

5. The non-invasive method of evaluating blood cell measurement of claim 1, further comprising providing a previous blood cell measurement value from previous blood test report, wherein the previous blood cell measurement value is used as a parameter for predicting the blood cell measurement with the processed dialysis tubing image datum in the image preprocessing step.

6. The non-invasive method of evaluating blood cell measurement of claim 1, wherein the image preprocessing step further comprises describing a feature of the processed dialysis tubing image datum by a statistical distribution model.

7. The non-invasive method of evaluating blood cell measurement of claim 1, further comprising performing a model building step, wherein the model building step comprises:

providing a reference dialysis tubing image database, wherein the reference dialysis tubing image database comprises a plurality of reference dialysis tubing image data, and each of the reference dialysis tubing image data comprises a reference color correction image and a reference dialysis tubing image;

performing a pre-training image processing step, wherein a color of the reference dialysis tubing image is corrected with the reference color correction image to obtain a plurality of reference processed dialysis tubing image data; and performing a training step, wherein a machine learning algorithm module is trained with the reference processed dialysis tubing image data until a loss function to converge to obtain the machine learning model.

8. The non-invasive method of evaluating blood cell measurement of claim 7, wherein the pre-training image processing step further comprises cropping the reference color correction image and the reference dialysis tubing image along edges thereof.

9. The non-invasive method of evaluating blood cell measurement of claim 7, wherein the pre-training image processing step further comprises a background correction for reducing an ambient light source differences in the reference dialysis tubing image.

10. The non-invasive method of evaluating blood cell measurement of claim 7, wherein the pre-training image processing step further comprises describing a feature of the processed dialysis tubing image data by a statistical distribution model.

11. The non-invasive method of evaluating blood cell measurement of claim 7, further comprising providing a previous reference blood cell measurement value from previous blood test report, wherein the previous reference blood cell measurement value is used as a parameter for training the machine learning algorithm module with the reference processed dialysis tubing image data in the pre-training image processing step.

12. The non-invasive method of evaluating blood cell measurement of claim 7, wherein the machine learning algorithm module is a gradient descent algorithm.

13. A non-invasive blood cell measurement evaluating system, comprising:

an image capturing device for obtaining a dialysis tubing image datum of a subject, wherein the dialysis tubing image datum comprises a color correction image and a dialysis tubing image; and a processor electrically connected to the image capture device, wherein the processor comprises:

an image correcting program, comprising:

an image correcting module for correcting a color of the dialysis tubing image by the color correction image to obtain a processed dialysis tubing image datum; and a machine learning model electrically connected to the image correcting program, comprising:

a value predicting unit using the processed dialysis tubing image datum to predict a blood cell measurement, so as to obtain a blood cell measurement value; and an evaluating unit predicting the blood cell measurement value and comparing with a threshold to output a blood cell measurement evaluation result, wherein the blood cell measurement value comprises a hemoglobin concentration value and a white blood cell count, and the threshold comprises a hemoglobin concentration threshold and a white blood cell count threshold, when the hemoglobin concentration value is less than or equal to the hemoglobin concentration threshold, the subject is determined to be required to undergo a relevant treatment to increase the hemoglobin concentration, when the hemoglobin concentration value is greater than the hemoglobin concentration threshold, the subject is determined not to be required to undergo the relevant treatment to increase the hemoglobin concentration, or to reduce or maintain an ongoing relevant treatment for increasing the hemoglobin concentration, and when the white blood cell count is greater than or equal to the white blood cell count threshold, the subject is determined to be required to treat for infection.

14. The non-invasive blood cell measurement evaluating system of claim 13, wherein the image correcting program further comprises an image cropping module for cropping the color correction image and the dialysis tubing image along edges thereof.

15. The non-invasive blood cell measurement evaluating system of claim 13, wherein the image correcting module further reduces ambient light source differences in the dialysis tubing image.

16. The non-invasive blood cell measurement evaluating system of claim 13, wherein the machine learning model is trained by a machine learning algorithm module.

17. The non-invasive blood cell measurement evaluating system of claim 16, wherein the machine learning algorithm module is a gradient descent algorithm.

18. The non-invasive blood cell measurement evaluating system of claim 13, wherein the processor further comprises a database comprising a previous blood cell measurement value from previous blood test report, and the machine learning model uses the previous blood cell measurement value as a parameter to predict the blood cell measurement with the processed dialysis tubing image datum.

19. The non-invasive blood cell measurement evaluating system of claim 14, wherein the image cropping module further comprises a statistical distribution model to describe a feature of the processed dialysis tubing image data.

* * * * *